United States Patent [19]

Boulogne et al.

[11] 4,108,185

[45] Aug. 22, 1978

[54] GREASELESS COSMETIC ARTICLE FOR APPLYING MAKE-UP TO THE EYELIDS

[75] Inventors: Jean P. Boulogne, L'Hay-les-Roses; Thibaud Hochmann, Champigny-sur-Marne; Jacques Michelet, Longjumeau; Bruno P. Morane, Paris, all of France

[73] Assignee: L'Oreal, Paris, France

[21] Appl. No.: 752,806

[22] Filed: Dec. 20, 1976

[30] Foreign Application Priority Data

Jan. 28, 1976 [FR] France .................................. 76 02282

[51] Int. Cl.² ............................................. A45D 33/00
[52] U.S. Cl. ........................................ 401/88; 424/63; 132/82 A
[58] Field of Search ................. 132/7, 82; 424/63, 64, 424/69, 33, 34, 6

[56] References Cited

U.S. PATENT DOCUMENTS 2,373,933  4/1945  Weeks ...................................... 424/63
3,471,611  10/1969  Scott et al. ............................... 424/6

OTHER PUBLICATIONS

E. Sagarin – Cosmetics – Science & Technology – 3/1972, p. 324.

*Primary Examiner*—Louis G. Mancene
*Assistant Examiner*—Gregory E. McNeill
*Attorney, Agent, or Firm*—Brisebois & Kruger

[57] ABSTRACT

Cosmetic article comprises a solid support coated with an impregnating layer which carries a coating layer. The impregnating layer comprises at least one hydro-soluble polymer and the coating layer comprises a product which is thixotropic in aqueous suspension, a polymeric binder capable of forming a gel in an aqueous medium when mixed with said thixotropic product, and a mixture of cosmetic powders.

18 Claims, No Drawings

GREASELESS COSMETIC ARTICLE FOR APPLYING MAKE-UP TO THE EYELIDS

SUMMARY OF THE INVENTION

There are a number of products for applying make-up to the skin, that is to say, for depositing a colored and/or nacreous layer on the skin, which make it possible to obtain an aesthetic effect. Cosmetic products of this type must have a sufficient softness of application and must permit precise distribution of the cosmetic product.

In the particular case of eyelid make-up, products are presently on the market which permit indirect appliction, that is to say, application by means of an applicator which may be a brush, a sponge, or the finger of the user. This method of operation nevertheless has a disadvantage in that the cosmetic powders become detached from the applicators during the make-up process and this results in substantial losses and soiling of the clothing.

It has accordingly been suggested, in order to avoid the disadvantages of indirect make-up, to utilize applicators permitting the user to apply the product directly to the skin to be made up. For this purpose, it is necessary that the cosmetic product have a sufficient strength so that it is not broken during the course of application. Make-up sticks or crayons permitting multiple applications have already been suggested for this purpose, but it has been, in general, found that it is particularly desirable to provide cosmetics which include a sufficient quantity of cosmetic for one complete make-up operation, but which may be discarded after the completion oof one operation. In particular, it has already been proposed that small sticks or strips of cardboard like matches be used, in which the end carries a cosmetic product in a quantity sufficient to make up the two eyelids of a user.

Cosmetic articles adapted to be directly used only a single time and which are presently on the market have their ends coated with a greasy cosmetic carried by an impregnating layer generally consisting of paraffin. The greasy cosmetics permit making-up under conditions of softness which are satisfactory, but their hardness depends upon the ambient temperature, which may lead to regrettable results if the temperature is too high, because the greasy base substance causes excessive softening of the cosmetic. Moreover, the adherence of the make-up to the eyelids is not satisfactory because the greasy colored base becomes concentrated in the creases of the eyelid. If an attempt is made to avoid excessive softening of the greasy cosmetic in the case of an increase in the ambient temperature, the cosmetic has an increased hardness and waxiness during application so that it does not spread well on the surface of the skin to be made up.

It is the object of the present invention to describe a make-up article comprising a sufficient quantity of cosmetic for a single application and which may be discarded after that application, the cosmetic consisting of a greaseless make-up product which permits the avoidance of all the disadvantages due to the presence of a greasy substance in the make-up product. The use of a greaseless cosmetic leads to significant difficulties because such a cosmetic does not adhere well to the support on which it is carried, for example, a stick or strip of cardboard, even if the precaution of coating this support with a sub-layer such as the one presently used for cosmetics containing a greasy product is taken. It has been found that a greaseless cosmetic does not adhere well on paraffin so that the cosmetic often becomes detached from its support long before application. In accordance with the invention it has been suggested that the support be coated with an impregnating layer different from that which has heretofore been used and that the latter impregnating layer be then coated with a composition which permits satisfactory attachment to the impregnating layer which has first been applied.

It is therefore an object of the present invention to provide a new article of manufacture which consists of a make-up member permitting the use of a greaseless cosmetic and adapted to direct application, said member comprising a solid support at least partially coated with an impregnating layer carrying a cosmetic product and characterized by the fact that the impregnating layer consists of at least one hydrosoluble polymer which is deposited in solution on said support, said impregnating layer being at least partially covered by a coating consisting of a homogeneous mixture comprising:

*a.* A product the aqueous suspensions of which are thixotropic;

*b.* A polymeric binder adapted to form a gel in an aqueous medium, said binder forming, when it is mixed with the thixotropic product of *a*, in an aqueous medium, a thixotropic mixture having a high viscosity;

*c.* A mixture of cosmetic powders comprising at least one pigment.

One of the essential characteristics of the polymer which constitutes the impregnating layer which is deposited on the support of the make-up article according to the invention, is that of being hydrosoluble. In effect, the application of the coating layer must be capable of causing partial redissolution of the surface of the impregnating layer so that the impregnating polymer assures, as a consequence of this partial redissolution, good adherence of the coating layer to the impregnating layer.

However, the impregnating polymer must not be too hydrosoluble because, if the redissolution of this polymer, at the moment of application of the coating layer, is too great, there will be an insufficient amount of the impregnating layer remaining on the supporting surface so that the adherence of the coating to the support would be considerably diminished. Moreover, if the impregnating polymer is too hydrosoluble, it migrates in the coating layer when that layer is applied, so that it surrounds the powders contained in the coating layer and the disintegration of this layer, at the moment of application to the skin to be made up, becomes insufficient. Moreover, if the impregnating polymer is too hydrosoluble and the coating layer is applied by soaking, the solution destined to constitute the coating layer is polluted by the passage of impregnating polymer into that solution.

It is consequently clear that one of the essential characteristics of the invention is the application of the impregnating layer and the coating layer in two separate steps because if an attempt were made to apply both products in a mixture, in the course of a single coating by soaking the impregnating polymer would coat the particles of the make-up so that the cosmetic would not come off well enough to produce a satisfactory make-up.

In a preferred embodiment the impregnating layer is made of a polymer the cloud point of which in a hydroethanolic solution at ambient temperature is attained if the water-ethanol proportion by weight in the polymeric solution is less than 1/0.66.

It has been found that particularly advantageous results are obtained when the impregnating polymer is selected from the group consisting of (1) the polyvinyl pyrrolidone/vinyl acetate copolymers; (2) the quaternary polymers of vinyl pyrrolidone and a copolymerizable vinylic monomer of the type described in French Pat. No. 2.077.417 and more particularly, polymers comprising (in molar proportions) from 40 to 90% vinyl pyrrolidone, 5 to 40% acrylate or methacrylate of di-(lower alkyl)-aminohydroxyalkyl, and 0 to 50% of a vinyl monomer copolymerizable with vinyl pyrrolidone, these polymers being, for example, of the type sold under the trademark "GAFQUAT 734"; and (3) acrylic copolymers of the type sold under the trademark "RESIN 2261" sold by the National Starch Company. When a polyvinyl pyrrolidone-vinyl acetate polymer is used it is preferred to use a polymer comprising 25 to 35% by weight of polyvinyl pyrrolidone and 75 to 65% by weight of vinyl acetate.

When a strip of cardboard like a matchstick is used as the support, the deposit of the impregnating polymer strengthens the cardboard and prevents it from bending at the moment of application. One may therefore advantageously impregnate the strip of cardboard throughout its length even though the strip will carry the cosmetic only at one end.

It has also been found that another essential characteristic of the invention consists in the presence of a thixotropic product in the mixture destined to constitute the coating layer. This mixture is made in the form of an aqueous suspension and the previously impregnated supports are soaked therein to take up the desired quantity of coating layer, said layer being subsequently dried. It is essential that the aqueous suspension which produces the coating layer contain a thixotropic product in order to avoid rapid deposit of the powders and pigments which the coating layer must contain, these powders and pigments having in general different densities and depositing rapidly when the aqueous suspension which produces the coating layer is not thixotropic and sufficiently viscous. Moreover, it is necessary that the coating layer contain a polymeric binder capable of insuring cohesion of the coating layer and preventing too ready a separation of the powders at the moment of application. In accordance with the invention the aqueous suspension which permits the coating layer to be obtained contains, in combination a thixotropic product and a polymeric binder, the mixture of which produces a viscous suspension. However, the quantity of polymeric binder need not be very large in this aqueous solution, since otherwise the separation of the cosmetic at the moment of application would be insufficient.

It has been found that particularly advantageous results are obtained by using as the thixotropic product an aqueous suspension of bentonite or an aqueous suspension of silicates of magnesium and aluminum in colloidal form, such as the one which may be obtained with the product sold under the trademark VEEGUM. As polymeric binder, it has been found that cationic derivatives of cellulose may be advantageously used, in particular those described in U.S. Pat. No. 3,472,840, and especially cellulose ethers containing a quaternary nitrogen and having the formula:

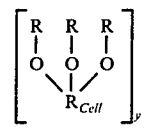

in which formula $R_{Cell}$ is the residue of an anhydroglucose, $y$ is an integer having a value between about 50 and about 20,000, and each radical R, taken individually, represents a substituted group responding to the general formula

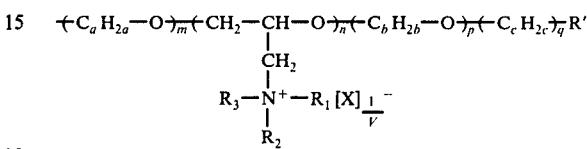

in which $a$ and $b$ are integers having a value of 2 or 3, $c$ is an integer having a value of 1 to 3, $m$ and $p$ are integers having a value of 0 to 10, $n$ is an integer having a value of 0 to 3, $q$ is an integer having the value 0 or 1, $R'$ is a constituent selected from the group consisting of

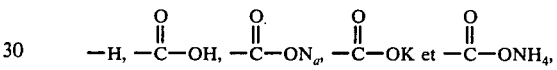

with the restriction that $q$ is equal to 0 when $R'$ is hydrogen, $R_1$, $R_2$ and $R_3$, taken individually, represent a constituent selected from the group formed by the alkyl, aryl, aralkyl, alkaryl, cycloalkyl, alkoxyalkyl and alkoxyaryl radicals, each of which $R_1$, $R_2$ and $R_3$ radicals may contain up to 10 carbon atoms provided that, if the constituent selected from the group is an alkoxyalkyl radical, there are at least two carbon atoms separating the hydrogen and nitrogen atoms, and also provided that the total number of carbon atoms in the radicals represented by $R_1$, $R_2$ and $R_3$ lies between 3 and 12 inclusive, while $R_1$, $R_2$ and $R_3$ and the nitrogen atom to which they are connected may form a heterocycle selected from the group consisting of pyridine, alphamethyl-pyridine, 2,5-diethyl-pyridine, 2,4,6-trimethyl-pyridine, N-methyl-piperidine, N-ethyl-piperidine, N-methyl-morpholine and N-ethyl-morpholine, X being an anion and V being an integer equal to the valence of X, the average value of $n$ per anhydroglucose unit of said cellulose ether being about 0.01 to about 1 and the average value of $m + p + q$ per anhydroglucose unit of said cellulose ether being about 0.01 to about 4. Among the cationic derivatives of cellulose one may use, for example, the polymer sold under the trademark "JR 400" by the Union Carbide Company. As a polymeric binder it has been found that one may also advantageously use carboxyvinyl polymers having a high molecular weight such as the one sold under the trademark "CARBOPOL 934".

The mixture of powders in the coating layer comprises in general at least one powder selected from the group formed by talc, rice starch, or corn starch, whether etherified or not. This mixture of powders also advantageously comprises at least one pigment taken from the group consisting of calcium carbonate, titanium oxide, and bismuth oxychloride. The mixture of powders comprises in particular, in the case of eye shadow, at least one colored pigment.

To insure good homogeneity of the suspension which produces the coating layer and to simultaneously insure a good separation of said layer at the moment of application without excessive crumbling, it has been found that one may advantageously use in the coating layer from 0.1 to 0.4% by weight of the polymeric binder in proportion to the total dry materials. Preferably the coating layer contains a bactericidal and fungicidal preserving agent.

The support which one may use for the make-up applicator according to the invention may be a stick of cardboard, wood, or plastic material. In the latter case, in order to facilitate the adherence of the impregnating layers and the coating, it is preferred to scarify the end of the stick which is to receive the coating. The stick may have the shape of a match and be sold in a packet containing a group of sticks, for example 12 or 24 detachable sticks, each stick being adapted to serve for one make-up operation and being discarded after this operation. In particular, the sticks may be cut from a strip of cardboard 44 mm wide to constitute detachable tongues 33 mm long and 3 mm wide, the cardboard having the thickness of about 1 mm. The impregnating layer may be deposited over a length of about 30 mm and the coating layer over a length of about 5 mm.

When the impregnating and coating layers are deposited by a soaking step, it has been found that best results are obtained by using relatively short dipping steps permitting the deposition of 0.03 to 0.06 mg/mm$^2$ of impregnating layer and 0.3 to 0.4 mg/mm$^2$ of coating layer, the weights being evaluated after drying the layers and the reference surfaces being measured with respect to the covered surface of the support.

It is also an object of the present invention to provide a new method of manufacturing a cosmetic article such as the one above described, said process consisting in coating a solid support with two successively deposited layers characterized by the fact that, in the first place, one soaks at least one part of the solid support in an impregnating solution containing a hydrosoluble polymer, dries the impregnating layer thus obtained, and in the second place, soaks the impregnated support in a suspension of coating material comprising, in homogenous mixture, on the one hand a thixotropic product, on the other hand a polymeric binder capable of forming a gel, and finally a mixture of cosmetic powders comprising at least one pigment, and that the coating layer thus deposited is then dried.

In a preferred method of carrying out the process above described, the impregnating solution is a hydroalcoholic solution and preferably a hydroethanolic solution. The suspension of the coating material is an aqueous suspension the viscosity of which is between 4 and 14 poises.

In order that the object of the invention may be better understood, there will now be described, purely by way of example, several methods of carrying it out.

First Step: Producing an impregnated support.

From a strip of cardboard 44 mm wide and 1 mm thick, tongues 33 mm long and 3 mm wide are cut to form a sort of comb. These tongues are immersed for a length of about 30 mm in a hydroethanolic solution having the following composition:

| | |
|---|---|
| Polyvinylpyrrolidone/vinyl acetate copolymer comprising 30% by weight of polyvinylpyrrolidone and 70% by weight of vinyl acetate in solution at 50% by weight in ethanol | 35 g |
| Ethyl alcohol at 96° | 65 g |

Soaking is continued for 3 seconds and the impregnated support is then dried at a temperature of 50° C for 50 minutes. It is found that 0.03 to 0.06 mg of polymer per mm$^2$ of support has been deposited.

Second Step: Producing a support having a coating layer on its end.

For a length of 5 mm the impregnated support obtained in the above first step is immersed in different aqueous suspensions the compositions of which are hereinafter given. The soaking continues for 3 seconds. The support with its coating is then dried for one hour at a temperature of 50° C. The aqueous suspensions used in the two examples of carrying out the invention which have been described are as follows:

| | | | |
|---|---|---|---|
| 1. | Thixotropic product: | | |
| | 5% suspension of magnesium and aluminum silicate (product VEEGUM) in de-ionized water | 12.28 | g |
| 2. | Polymeric binder: | | |
| | 2% solution in de-ionized water of a cationic cellulosic polymer sold by Union Carbide Company under the trademark "JR 400" and having (in a 2% aqueous solution) a viscosity of 25° C of 300 to 500 centipoises | 7 | g |
| 3. | Mixture of powders: | 35.09 | g |
| | This mixture comprises: | | |
| | Talc | 15.80 | g |
| | Bismuth oxychloride | 7.02 | g |
| | Etherified rice starch | 5.2 | g |
| | Titanium oxide | 1.75 | g |
| | Green pigment | 3.51 | g |
| | Blue pigment | 1.75 | g |
| 4. | De-ionized water | | |
| | containing 0.30% bactericidal and fungicidal preservative | 45.63 | g |

EXAMPLE 2

| | | | |
|---|---|---|---|
| 1. | Thixotropic products: | | |
| | Bentonite | 1.20 | g |
| 2. | Polymeric binder: | | |
| | 2% solution in de-ionized water of a cationic cellulosic polymer sold by Union Carbide under the trademark "JR 400" and having (in 2% aqueous solution) a viscosity at 25° C of 300 to 500 centipoises | 2 | g |
| 3. | Mixture of powders: | 39.80 | g |
| | Distributed as follows: | | |
| | Talc | 4.0 | g |
| | Calcium carbonate | 22.55 | g |
| | Titanium oxide | 8 | g |
| | Green pigment | 3.50 | g |
| | Blue pigment | 1.75 | g |
| 4. | De-ionized water | | |
| | comprising 0.3% of bactericidal and fungicidal preservative | 57.0 | g |

It has been found that, in the two examples which have just been given, the cosmetic articles obtained permit a very satisfactory application of the make-up. The cosmetic comes off sufficiently but not excessively. The cosmetic does not crumble in the course of application. The coating layer has a uniform color which shows that the impregnating polymer has not migrated into the coating layer.

It will of course be appreciated that the embodiments which have been described have been given purely by way of illustration and example and may be modified as to detail without thereby departing from the basic principles of the invention.

What is claimed is:

1. In a cosmetic article for directly applying a greaseless cosmetic, said article comprising a solid support coated with at least one impregnating layer carrying a coating layer containing a cosmetic, the improvement according to which the impregnating layer comprises at least one hydrosoluble polymer deposited in solution on the support, and said coating layer comprising a homogenous mixture containing
   (a) a product which is thixotropic in aqueous suspension;
   (b) a polymeric binder capable of forming a gel in an aqueous medium, said binder forming, when mixed with said thixotropic product in an aqueous medium, a thixotropic mixture having a high viscosity; and
   (c) a mixture of cosmetic powders comprising at least one pigment.

2. Cosmetic article as claimed in claim 1 in which the impregnating layer is a polymer the cloud point of which in hydroethanolic solution is reached at ambient temperature if the water/ethanol ratio by weight of the polymeric solution is less than 1/0.66.

3. Cosmetic article as claimed in claim 2 in which the impregnating polymer is selected from the group consisting of (1) polyvinyl pyrrolidone vinyl acetate copolymers; (2) the quaternary polymers of vinyl pyrrolidone and a copolymerizable vinylic monomer comprising (in molar proportions) 40 to 90% of vinyl pyrrolidone, 5 to 40% acrylate or methacrylate of di (lower alcohol) aminohydroxyalkyl, and 0 to 50% of a vinyl monomer copolymerizable with the vinyl pyrrolidone.

4. Cosmetic article according to claim 3 in which the impregnating polymer is a polyvinyl pyrrolidone/vinyl acetate polymer in which the impregnating polymer comprises 20 to 35% by weight of polyvinyl pyrrolidone and 75 to 65% by weight of vinyl acetate.

5. Cosmetic article as claimed in claim 1 in which the thixotropic product selected from the group consisting of an aqueous suspension of bentonite and an aqueous suspension of magnesium and aluminum silicates in colloidal form.

6. Cosmetic article as claimed in claim 1 in which the polymeric binder is selected from the group consisting of
   (1) cellulose ethers containing a quaternary nitrogen and having the formula

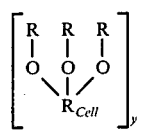

in which $R_{Cell}$ is the residue of an anhydroglucose, $y$ is a whole number having a value between about 50 and about 20,000, and each radical R, taken individually, represents a substituted group responding to the general formula

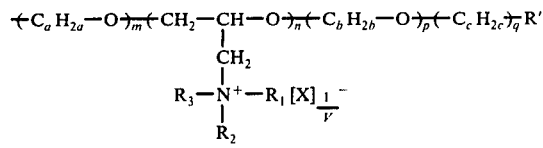

in which $a$ and $b$ are integers having a value of 2 or 3, $c$ is an integer having a value of 1 to 3, $m$ and $p$ are integers having a value of 0 to 10, $n$ is an integer havig a value of 0 to 3, $q$ is an integer having the values 0 or 1, R' is an element selected from the group formed by

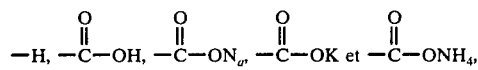

with the restriction that $q$ is equal to 0 when R' is hydrogen, $R_1$, $R_2$ and $R_3$, taken individually, represent a member selected from the group formed by the alkyl, aryl, aralkyl, alkaryl, cycloalkyl, alkoxyalkyl and alkoxyaryl radicals, with each of the radicals $R_1$, $R_2$ and $R_3$ containing up to 10 carbon atoms, provided that if the member selected from the group is an alkoxyalkyl radical there are at least two atoms of carbon separating the oxygen atoms from the nitrogen atom and also provided that the total number of the carbon atoms in the radicals represented by $R_1$, $R_2$ and $R_3$ is between 3 and 12, and in which $R_1$, $R_2$ and $R_3$ and the nitrogen atom to which they are connected may form a heterocycle selected from the group consisting of pyridine, alphamethyl-pyridine, 2,5-dimethyl-pyridine, 2,4,6-trimethyl-piperidine, N-methyl piperidine, N-ethyl-piperidine, N-methyl-morpholine and N-ethyl-morpholine, X being an anion, and V being an integer equal to the valence of X, the average value of $n$ per anhydroglucose unit of cellulose ether being about 0.01 to about 1, and the average value of $m + p + q$ per anhydroglucose unit of said cellulose ether being about 0.01 to about 4; and
   (2) carboxyvinyl polymers having a high molecular weight.

7. Cosmetic article according to claim 1 in which the mixture of powders in the coating layer comprises at least one powder selected from the group formed by talc, rice starch, or corn starch, whether etherified or not.

8. Cosmetic article according to claim 1 in which the mixture of powders in the coating layer comprises at least one pigment selected from the group consisting of calcium carbonate, titanium oxide and bismuth oxychloride.

9. Cosmetic article as claimed in claim 1 in which the mixture of powders in the coating layer comprises at least one colored pigment.

10. Cosmetic article according to claim 1 in which the coating layer comprises 1.5% to 4% by weight of polymeric binder in proportion to the total dry weight of the thixotropic product and 0.10% to 0.40% of polymeric binder by weight with respect to the dry total material of the coating.

11. Cosmetic article as claimed in claim 1 in which the coating layer contains a bactericidal and fungicidal preservative.

12. Cosmetic article according to claim 1 in which the support is a strip of cardboard, wood or plastic material.

13. Cosmetic article according to claim 12 in which the support is a piece of cardboard in which the piece has the shape of a strip impregnated over almost its entire length with the impregnating polymer.

14. Cosmetic article as claimed in claim 12, in which the support is a stick of plastic material characterized by the fact that the end of the stick which is to receive the coating material is scarified.

15. Cosmetic article as claimed in claim 1 which comprises 0.03 to 0.06 mg per $mm^2$ of impregnating layer and 0.3 to 0.4 mg per $mm^2$ of coating layer, the weights being evaluated after drying the layers and the reference surfaces being measured in comparison with the covered surface of the support.

16. In a process of making a cosmetic article according to claim 1, said process consisting in coating a solid support with two successive deposited layers the improvement according to which at least part of the solid support is dipped in an impregnating solution containing a hydrosoluble polymer, the impregnating layer is then dried, the impregnating support is then dipped in a suspension of coating material comprising in homogenous mixture a thixotropic product, a polymeric binder capable of forming a gel, and a mixture of cosmetic products comprising at least one pigment, and the coating layer thus deposited is then dried.

17. Process as claimed in claim 16, in which the impregnating solution is a hydroalcoholic solution.

18. Process as claimed in claim 16 in which the coating material suspension is an aqueous suspension the viscosity of which lies between 4 and 14 poises.

* * * * *